United States Patent
Tylutki et al.

(10) Patent No.: US 9,562,841 B2
(45) Date of Patent: Feb. 7, 2017

(54) ENGINE OUTPUT SOOT DIAGNOSTIC CONTROL SYSTEM BASED ON TRANSIENT DRIVE CYCLE DETECTION

(71) Applicant: GM GLOBAL TECHNOLOGY OPERATIONS LLC, Detroit, MI (US)

(72) Inventors: Vincent J. Tylutki, Livonia, MI (US); John Coppola, Pinckney, MI (US); Christopher Whitt, Howell, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 221 days.

(21) Appl. No.: 14/450,945

(22) Filed: Aug. 4, 2014

(65) Prior Publication Data

US 2016/0033385 A1 Feb. 4, 2016

(51) Int. Cl.
- *F02D 41/22* (2006.01)
- *F02D 45/00* (2006.01)
- *G01N 15/06* (2006.01)
- *F02D 41/04* (2006.01)
- *F02D 41/14* (2006.01)
- *G01N 15/00* (2006.01)
- *F02D 41/24* (2006.01)

(52) U.S. Cl.
CPC ......... *G01N 15/0656* (2013.01); *F02D 41/045* (2013.01); *F02D 41/1467* (2013.01); *F02D 41/22* (2013.01); *F02D 41/2403* (2013.01); *G01N 2015/0046* (2013.01); *Y02T 10/40* (2013.01)

(58) Field of Classification Search
CPC .......... F02D 41/00; F02D 41/02; F02D 41/04; F02D 41/045; F02D 41/1467; F02D 41/22; F02D 41/2403; G01N 15/0655; G01N 2015/0046
See application file for complete search history.

(56) References Cited

U.S. PATENT DOCUMENTS

| | | | |
|---|---|---|---|
| 2007/0125349 A1* | 6/2007 | Zanini-Fisher | F01N 11/00 123/679 |
| 2009/0118988 A1* | 5/2009 | Moening | F02D 41/123 701/109 |
| 2010/0180576 A1* | 7/2010 | Wang | F01N 3/2066 60/276 |
| 2011/0203348 A1* | 8/2011 | Hedayat | G01N 15/0656 73/23.33 |
| 2012/0117942 A1* | 5/2012 | Kowalkowski | F02D 41/146 60/273 |
| 2013/0317727 A1* | 11/2013 | Kowalkowski | F02D 41/123 701/112 |

(Continued)

*Primary Examiner* — Nguyen Ha
(74) *Attorney, Agent, or Firm* — Cantor Colburn LLP

(57) ABSTRACT

An internal combustion engine control system including an internal combustion engine including at least one cylinder configured to perform combustion of an air/fuel mixture therein during a drive cycle. An electronic engine control module is configured to selectively execute at least one soot-based diagnostic operation that diagnoses the internal combustion engine based on exhausted soot. An electronic diagnostic evaluation module is in electrical communication with the engine control module and is configured to disable the at least one soot-based diagnostic operation based on at least one transient drive event of the internal combustion engine during the drive cycle.

12 Claims, 2 Drawing Sheets

(56) References Cited

U.S. PATENT DOCUMENTS

| | | | | |
|---|---|---|---|---|
| 2013/0327018 A1* | 12/2013 | Tylutki | .................... | F01N 11/00 60/274 |
| 2014/0067179 A1* | 3/2014 | Amano | .................. | B60K 6/442 701/22 |
| 2014/0067200 A1* | 3/2014 | Amano | .................. | B60K 6/442 701/34.4 |
| 2014/0069081 A1* | 3/2014 | Tylutki | .................. | F01N 11/002 60/274 |
| 2014/0144126 A1* | 5/2014 | Kowalkowski | ......... | F01N 3/208 60/274 |
| 2015/0088398 A1* | 3/2015 | Cui | ......................... | F01N 11/00 701/101 |
| 2015/0354485 A1* | 12/2015 | Santillo | .................. | F02D 41/22 701/104 |

* cited by examiner

ENGINE OUTPUT SOOT DIAGNOSTIC CONTROL SYSTEM BASED ON TRANSIENT DRIVE CYCLE DETECTION

FIELD OF THE INVENTION

The subject invention relates generally to internal combustion engine control systems, and more particularly, to internal combustion engine diagnostic systems.

BACKGROUND

Exhaust gas generated from combusting an air/fuel mixture stored in a cylinder of an internal combustion engine is a heterogeneous mixture that contains gaseous carbon emissions such as, but not limited to, carbon monoxide ("CO"), unburned hydrocarbons and oxides of nitrogen ("$NO_x$") as well as particulate matter and soot comprising condensed phase materials (liquids and solids).

Vehicles typically include exhaust gas treatment systems that include one or more exhaust treatment devices such as, for example, a particulate filter. The particulate filter includes a filter substrate that is disposed in fluid communication with the exhaust gas. The filter substrate is configured to collect the particulate matter and soot as the exhaust gas flow therethrough.

Federally mandated engine output performance requirements are becoming stricter as concerns regarding carbon emissions continue to increase. Engine out soot models are typically used to estimate engine soot output, which in turn is used diagnose the in-use performance of an internal combustion engine and the particular filter. Conventional engine out soot models, however, may not estimate engine soot output with the accuracy needed to satisfy federally mandated in-use rate performance requirements. When operating an internal combustion engine in transient conditions, for example, conventional engine out soot models in combination with particular matter sensors can result in a false failing diagnosis or potentially false passing diagnosis.

SUMMARY OF THE INVENTION

In one exemplary embodiment of the invention, an internal combustion engine control system comprises an internal combustion engine including at least one cylinder configured to perform combustion of an air/fuel mixture therein during a drive cycle. An electronic engine control module is configured to selectively execute at least one soot-based diagnostic operation that diagnoses the internal combustion engine based on exhausted soot. An electronic diagnostic evaluation module is in electrical communication with the engine control module and is configured to disable the at least one soot-based diagnostic operation based on at least one transient drive event of the internal combustion engine during the drive cycle.

In another exemplary embodiment of the invention, a method of controlling a diagnostic system of an internal combustion engine, the method comprising combusting an air/fuel mixture in a cylinder of the internal combustion engine during a drive cycle. The combustion generates soot that is exhausted from the cylinder. The method further includes selectively performing at least one soot-based diagnostic operation that diagnoses the internal combustion engine based on the exhausted soot. The method further includes disabling the at least one soot-based diagnostic operation based on at least one transient drive event of the internal combustion engine during the drive cycle.

The above features of the invention are readily apparent from the following detailed description of the invention when taken in connection with the accompanying drawings.

BRIEF DESCRIPTION OF THE DRAWINGS

Other features and details appear, by way of example only, in the following detailed description of embodiments, the detailed description referring to the drawings in which.

DESCRIPTION OF THE EMBODIMENTS

Figure 1:
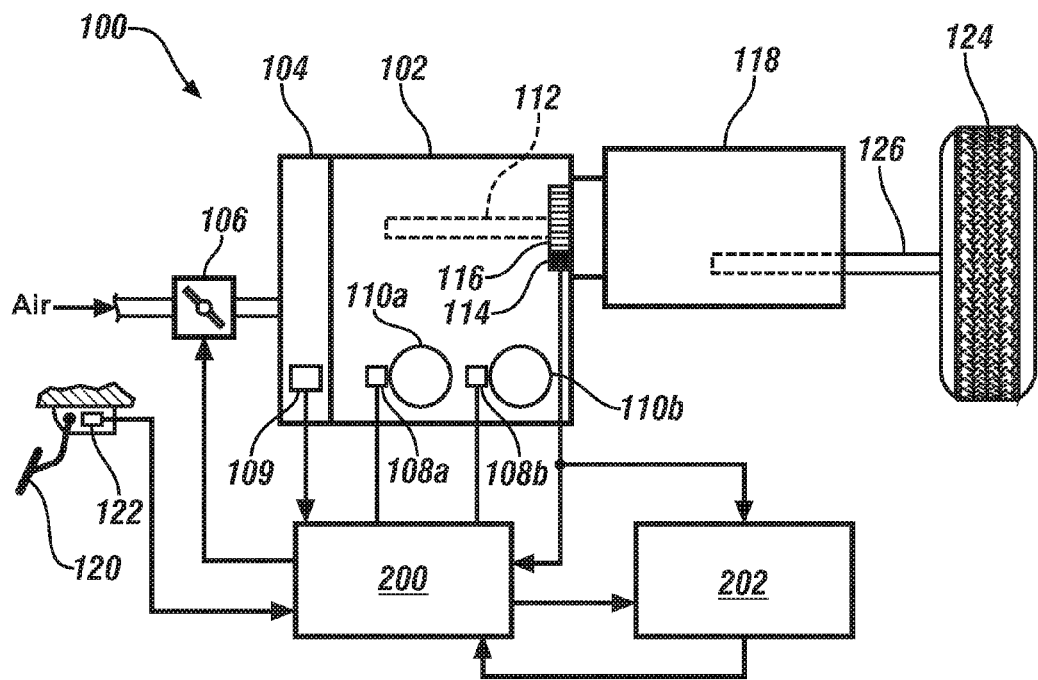
FIG. 1 is a functional block diagram illustrating a vehicle system according to an exemplary embodiment of the present disclosure.

The following description is merely exemplary in nature and is not intended to limit the present disclosure, its application or uses. It should be understood that throughout the drawings, corresponding reference numerals indicate like or corresponding parts and features. As used herein, the term module refers to processing circuitry that may include an application specific integrated circuit (ASIC), an electronic circuit, a processor (shared, dedicated, or group) and memory that executes one or more software or firmware programs, a combinational logic circuit, and/or other suitable components that provide the described functionality.

Referring to FIG. 1, a functional block diagram of a vehicle system 100 is illustrated according to an exemplary embodiment. The vehicle system 100 includes an engine 102 configured to generate a rotational torque. For purposes of discussion only, the engine 102 will be discussed as a diesel-type internal combustion engine. It is appreciated, however, that vehicle system 100 may be utilized with other types of internal combustion engines including, but not limited to, spark-ignition (e.g., gasoline-type) internal combustion engines. One or more systems and/or actuators of the engine 102 may be controlled by an engine control module (ECM) 200 as described in greater detail below.

Air is drawn into the engine 102 through an intake manifold 104. The ECM 200 is configured to control one or more fuel injectors 108a/108b to deliver a quantity of fuel to one or more cylinders 110a/110b where it is mixed with air to form a combustible air/fuel mixture. According to an embodiment, the ECM 200 is also configured to control a throttle valve 106. In cases where the engine is a diesel engine, for example, the throttle valve may be used to generate an intake manifold vacuum, thereby recirculating exhaust gas into cylinders 110a/110b. This technique is typically referred to as exhaust gas recirculation (EGR), and may lower combustion temperatures and reduce NOx production as understood by one of ordinary skill in the art. According to an embodiment, individual actuator modules (e.g., a throttle actuator module and a fuel actuator module) may be provided to control the throttle valve 106 and one or more of the fuel injectors 108a/108b, respectively. A mass air flow (MAF) sensor 109 may output a mass air signal indicating the quantity of air delivered into the intake manifold 104.

Each cylinder 110a/110b includes a piston (not shown) that is coupled to a crankshaft 112. Combustion of the air/fuel mixture may include four-strokes: an intake stroke, a compression stroke, a combustion (or expansion) stroke, and an exhaust stroke. During the intake stroke, the piston is lowered to a bottom-most position, for example, and the air and fuel are introduced into the cylinder 110a/110b, etc. The bottom-most position may be referred to as a bottom dead center (BDC) position.

During the compression stroke, the crankshaft 112 drives the piston toward a top-most position, for example, thereby compressing the air/fuel mixture within the cylinders 110a/110b, etc. The top-most position may be referred to as a top dead center (TDC) position. Combustion of the air/fuel mixture drives the piston toward the BDC position, thereby rotatably driving the crankshaft 112. This rotational force (i.e., torque) may be the compressive force that compresses the air/fuel mixture during the compression stroke of a next cylinder in a predetermined firing order of the cylinders 110a/110b, etc. Exhaust gas resulting from the combustion of the air/fuel mixture is expelled from the cylinder 110a/110b, etc. during the exhaust stroke.

An engine output speed (EOS) sensor 114 measures rotational speed of the crankshaft 112 and generates an EOS signal indicating the EOS. For example only, the EOS sensor 114 may include a variable reluctance (VR) sensor or another suitable type of EOS sensor 114. The gear 116 may include "N" number of teeth, and is configured to rotate with the crankshaft 112. The EOS sensor 114 generates a pulsed signal in response to detecting one or more of the teeth during rotation of the gear 116. The time period between each pulse (i.e., between each detected tooth) may determine the overall speed of the crankshaft 112.

Each pulse of the signal may correspond to an angular rotation of the crankshaft 112 by an amount equal to 360° divided by N teeth. For example only, the gear 116 may include 60 equally spaced teeth (i.e., n=60) and each pulse may correspond to 6° of rotation of the crankshaft 112. In various implementations, one or more of the N equally spaced teeth may be omitted. For example only, two of the N teeth may be omitted. The one or more teeth may be omitted, for example, as an indicator of one revolution of the crankshaft 112. The EOS sensor 114 may generate the EOS based on a time period between the pulses, i.e., between each sensed tooth. For example only, the EOS sensor 114 may generate the EOS based on a period that it takes the crankshaft 112 to rotate a predetermined angle (e.g., 90°) during the expansion stroke of the cylinders 110a/110b, etc. The EOS may be utilized to determine additional dynamic events (i.e., disturbances) of the crankshaft 112 including, but not limited to, acceleration/deceleration and/or knocking, which in turn indicates a disturbance of one or more cylinders 110a/110b, etc. For example, a disturbance of a cylinder 110a/110b, etc. may be determined based on a first derivative of the EOS (e.g., speed) measured during the combustion stroke of the cylinder 110a/110b, etc.

The engine 102 may transfer the torque output to a transmission 118 via the crankshaft 112. A position of an accelerator pedal 120, for example, can indicate a desired amount of torque as understood by one of ordinary skill in the art. A pedal sensor 122 is configured to detect a change in position of the accelerator pedal 120. Based on the position of the accelerator pedal 120, the pedal sensor 122 outputs a pedal signal that indicates a driver's desired vehicle speed and thus fuel consumption necessary to perform various driving maneuvers. The position of accelerator pedal 120 further commands the ECM 200 to control various engine actuators and output the desired torque from the pistons. For example, the ECM 200 analyzes the pedal signal and determines an amount of air and/or fuel quantity needed to obtain the desired torque output. Based on the determined amount of air and fuel, the ECM 200 adjusts the throttle valve 106 to regulate airflow into the engine intake manifold 104. The ECM 200 can further control the fuel injectors 108a/108b to regulate the timing and/or quantity of fuel injected into the cylinders 110a/110b. It is appreciated that various other actuators and/or engine parameters may be adjusted to obtain the desired output torque.

The ECM 200 further controls the transmission 118 such that the desired output torque from the pistons is transferred to one or more wheels 124 via a transmission output shaft 126. In this manner, the driver's desired speed can be obtained. In the case where the transmission 118 is an automatic-type transmission, the vehicle system 100 may include a torque transfer device, such as a torque converter, that transfers the output torque to the transmission 118.

The vehicle system 100 further includes an electronic EOS diagnostic control module 202 in electrical communication with the EOS sensor 114 and the ECM 200. According to an embodiment, the EOS diagnostic control module 202 is configured to detect one or more transient drive events occurring during a drive cycle of the engine 102. When the number of transient drive events exceeds a threshold, the EOS diagnostic control module 202 determines that an excessive number of transient drive events exists and disables one or more soot dependent diagnostics. By disabling the soot dependent diagnostics in response to detecting an excessive number of transient drive events, the possibility of misdiagnosing engine soot output performance is reduced.

Figure 2:
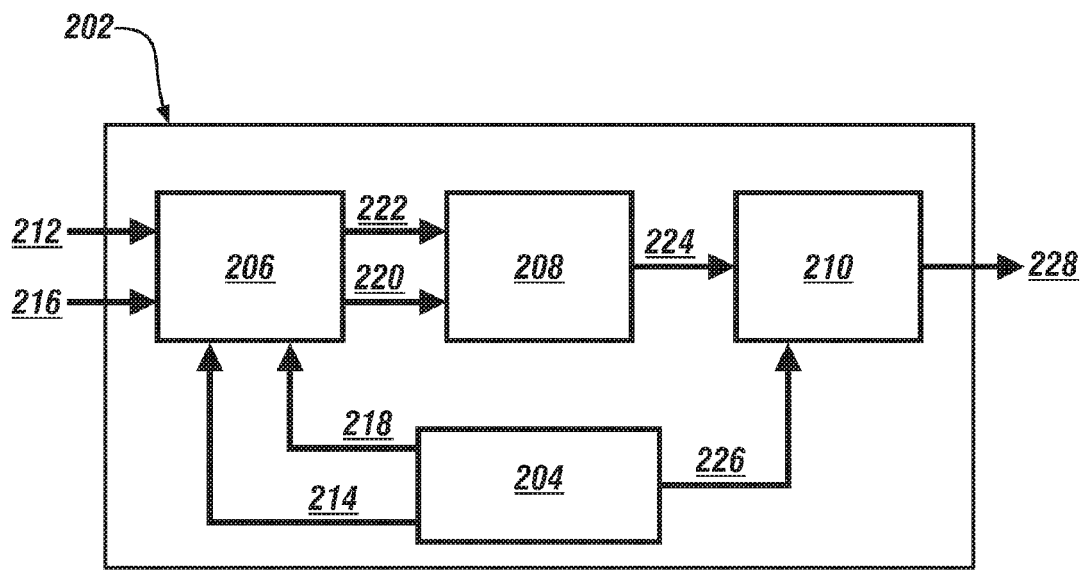
FIG. 2 is a functional block diagram illustrating an engine out soot model diagnostic control module according to an exemplary embodiment of the present disclosure.

Turning now to FIG. 2, a functional block diagram of an electronic EOS diagnostic control module 202 is illustrated according to an exemplary embodiment of the present disclosure. The EOS diagnostic control module 202 includes an electronic memory unit 204, an electronic transient detection module 206, an electronic transient event counter module 208, and an electronic diagnostic evaluation module 210.

The memory unit 204 stores one or more threshold values, time periods over which to sample the fuel quantity, a number of configurable limits, maps, data values, variables, temperature models, engine out soot models, and system models. In this manner, one or more of the sub-modules 206-210 may retrieve the requisite parameters and threshold values necessary to generate a respective output signal used to determine whether one or more soot dependent diagnostics should be disabled during a particular drive cycle.

The transient detection module 206 receives an initial transient input signal 212 which is used to detect the occurrence of a transient drive event. According to an embodiment, the transient input signal 212 is a fuel quantity signal 212 indicating an amount of fuel injected by the fuel injectors 108a/108b. It is appreciated, however, that the transient input signal 212 may also be a mass air signal output from the MAF sensor 109, or a combination of a fuel quantity signal and the mass air signal. The fuel quantity signal 212, for example, is sampled over a time period value 214 retrieved from the memory unit 204 to determine an absolute gradient value which indicates a deceleration or acceleration of the engine 102.

In response to determining a deceleration or acceleration of the engine 102, the transient detection module 206 determines whether the detected deceleration or acceleration is a result of a transient drive event. According to an embodiment, the transient detection module 206 receives the EOS signal 216 output from the EOS sensor 114. The EOS signal 216 is then compared to a speed threshold value 218 retrieved from the memory unit 204. When the speed indicated by the EOS signal 216 is below the speed threshold value 218, the transient detection module 206 outputs a steady-state signal 220 indicating the engine 102 is operating at a steady-state condition. When, however, the speed indicated by the EOS signal 216 exceeds the speed threshold value 218, the transient detection module 206 outputs a transient detection signal 222 indicating the detection of a transient drive event.

The transient event counter module 208 compares the detected transient events with the detected steady-state events to normalize the overall number of detected transient events. When the number of transient events exceeds the number of stead-state events by a count threshold, a normalized transient event is determined and the transient event counter module outputs a transient event count signal 224.

The electronic diagnostic evaluation module 210 is in electrical communication with the transient event counter module 208 and increments a counter included therein in response to receiving each transient event count signal 224. The value of the counter is compared to a transient event threshold value 226 retrieved from the memory unit 204. When the number of counted transient event signals 224 (i.e., the number of detected transient events) exceeds the transient event threshold value 226, the electronic diagnostic evaluation module 210 determines that the drive cycle includes an excessive number of transient events, and outputs a diagnostic disable signal 228 that disables one or more soot-based diagnostic operations during the drive cycle. Accordingly, the possibility of misdiagnosing engine output soot performance of the engine 102 due to the occurrence of excessive transient events during the drive cycle is reduced.

Figure 3:
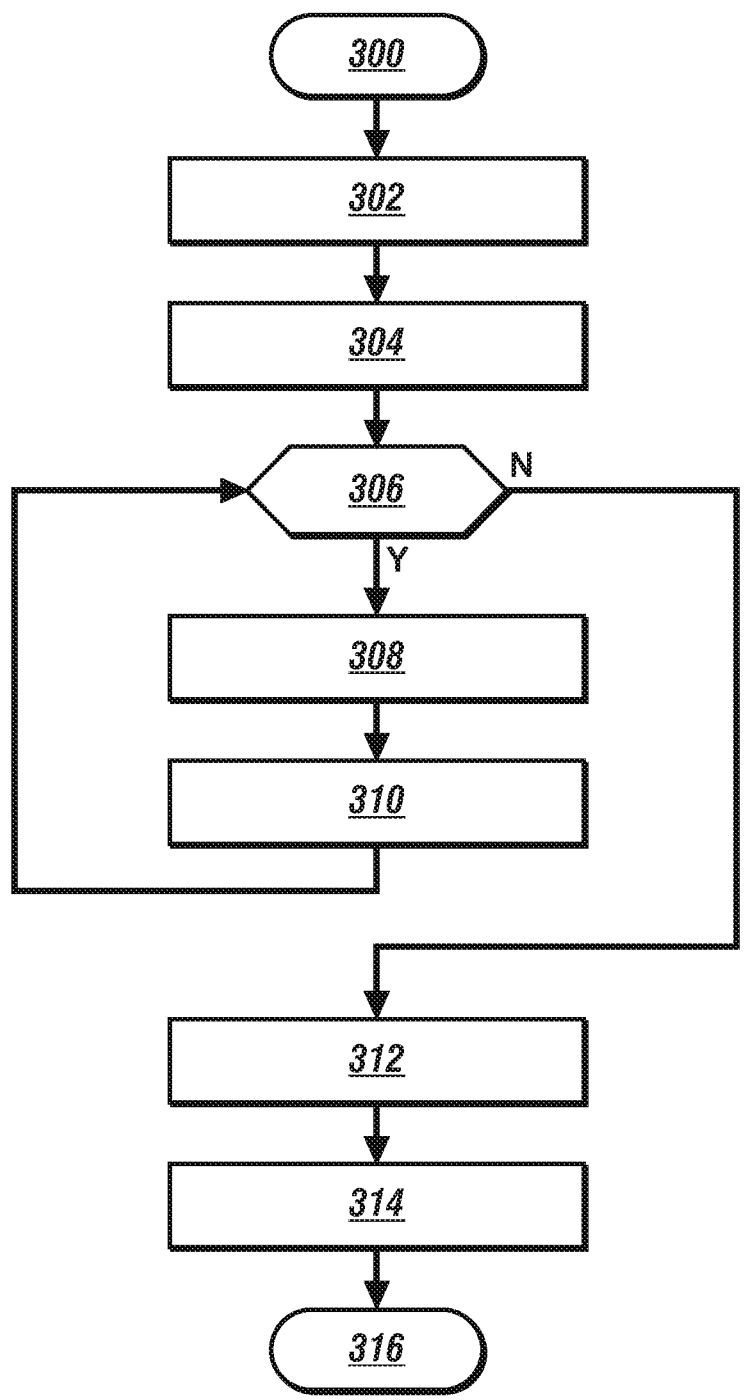
FIG. 3 is a flow diagram illustrating a method of controlling a diagnostic system included in a vehicle system according to an exemplary embodiment.

Turning now to FIG. 3, a flow diagram illustrates a method of controlling a diagnostic system included in a vehicle system according to an exemplary embodiment. The method begins at operation 300, and at operation 302 one or more drive cycles of an engine are monitored. At operation 304, one or more transient drive events are detected. At operation 306, the number of transient drive events is compared to a transient threshold value. When the number of transient drive events is below the transient threshold, a nominal drive cycle is determined at operation 308. At operation, 310, one or more soot dependent diagnostics (e.g., engine diagnostic operations based on engine output soot levels) are enabled, and the operation continues comparing the number of detected transient events to the transient threshold at operation 306.

When, however, the number of transient drive events exceeds the transient threshold, the drive cycle is determined to realize an excessive number of transient drive events at operation 312. At operation 314, the soot-based dependent diagnostics (e.g., engine diagnostic operations based on engine output soot levels) are disabled, and the method ends at operation 316. In this manner, a reduced risk of false failing and false passing diagnostics based on engine output soot measurements may be achieved. It is appreciated that the system and method described above may be modified to disable various other diagnostics that are based on models that may produce inaccurate measurements under specific engine operating conditions.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the application.

What is claimed is:

1. An internal combustion engine control system, comprising:
   an internal combustion engine including at least one cylinder configured to perform combustion of an air/fuel mixture therein during a drive cycle, the combustion generating soot that is exhausted from the at least one cylinder;
   an electronic engine control module configured to selectively execute at least one soot-based diagnostic operation that diagnoses the internal combustion engine based on the exhausted soot; and
   an electronic diagnostic evaluation module in electrical communication with the engine control module, the diagnostic evaluation module configured to disable the at least one soot-based diagnostic operation based on at least one transient drive event of the internal combustion engine during the drive cycle,
   wherein the diagnostic evaluation module compares a number of detected transient drive events to a transient threshold, and disables the at least one soot-based diagnostic operation when the number of detected transient drive events exceeds the transient threshold.

2. The internal combustion engine control system of claim 1, wherein the at least one transient drive event is detected based on at least one of a quantity of air and a quantity of fuel delivered to the cylinder.

3. The internal combustion engine control system of claim 2, wherein the transient event is detected based on a rate of change of the quantity of fuel over a sampled time period.

4. The internal combustion engine control system of claim 3, further comprising an engine output speed sensor that outputs an engine output speed signal indicating an engine speed of the internal combustion engine;
   wherein the diagnostic evaluation module is in electrical communication with the engine output speed sensor and determines the rate of change of the quantity of fuel corresponds to a transient drive event when the engine speed exceeds a speed threshold.

5. The internal combustion engine control system of claim 4, wherein the diagnostic evaluation module determines a steady-state drive event when the number of detected transient drive events is less than or equal to the transient threshold.

6. The internal combustion engine control system of claim 5, wherein the diagnostic evaluation module determines a plurality of steady-state drive events and a plurality of transient drive events, and outputs a normalized transient drive event based on a comparison between the a total number of the steady-state drive events detected over a normalized time period and a total number of the transient drive events detected over the normalized time period.

7. A method of controlling a diagnostic system of an internal combustion engine, the method comprising:
   combusting an air/fuel mixture in at least one cylinder of the internal combustion engine during a drive cycle, the combustion generating soot that is exhausted from the at least one cylinder;
   selectively performing at least one soot-based diagnostic operation that diagnoses the internal combustion engine based on the exhausted soot; and
   detecting at least one transient drive event of the internal combustion engine during the drive cycle, and disabling the at least one soot-based diagnostic operation in response to detecting the at least one transient drive event, wherein the detecting the at least one transient drive event further comprises comparing a number of detected transient drive events to a transient threshold, and disabling the at least one soot-based diagnostic operation in response to the number of detected transient drive events exceeding the transient threshold.

8. The method of claim 7, further comprising detecting the at least one transient drive event based on at least one of a quantity of air and a quantity of fuel delivered to the cylinder.

9. The method of claim 8, further comprising detecting the transient event based on a rate of change of the quantity of fuel over a sampled time period.

10. The method of claim 9, further comprising:
determining an engine speed of the internal combustion engine; and
determining the rate of change of the quantity of fuel corresponding to a transient drive event when the engine speed exceeds a speed threshold.

11. The method of claim 10, further comprising determining a steady-state drive event when the number of detected transient drive events is less than or equal to the transient threshold.

12. The method of claim 11, further comprising:
determining a plurality of steady-state drive events;
determining a plurality of transient drive events; and
determining a normalized transient drive event based on a comparison between the a total number of the steady-state drive events detected over a normalized time period and a total number of the transient drive events detected over the normalized time period.

* * * * *